(12) United States Patent
Fong et al.

(10) Patent No.: US 6,632,625 B1
(45) Date of Patent: Oct. 14, 2003

(54) MUTANT OB RECEPTORS AND NUCLEOTIDES ENCODING THEM

(75) Inventors: Tung M. Fong, Somerset, NJ (US); Ruey-Ruey C. Huang, Towaco, NJ (US); Leonardus Van Der Ploeg, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 08/982,430

(22) Filed: Dec. 2, 1997

Related U.S. Application Data (60) Provisional application No. 60/032,367, filed on Dec. 2, 1996.

(51) Int. Cl.$^7$ .......................... C12Q 1/66; C07K 14/705
(52) U.S. Cl. .......................... 435/8; 430/350; 536/23.5; 435/7.2; 435/7.21; 435/320.1; 435/325; 435/252.3
(58) Field of Search .............................. 435/69.1, 252.3, 435/320.1; 536/23.5

(56) References Cited

U.S. PATENT DOCUMENTS

| | | | |
|---|---|---|---|
| 4,857,637 A | | 8/1989 | Hammonds et al. |
| 5,401,629 A | | 3/1995 | Harpold et al. |
| 5,643,748 A | | 7/1997 | Snodgrass et al. |
| 5,972,621 A | * | 10/1999 | Tartaglia et al. .............. 435/7.1 |

FOREIGN PATENT DOCUMENTS

| | | |
|---|---|---|
| WO | WO 91/17252 | 11/1991 |
| WO | WO 96/08510 | 3/1996 |
| WO | WO 96/35787 | 11/1996 |
| WO | WO 97/26335 | 7/1997 |

OTHER PUBLICATIONS

Lee et al., "Abnormal splicing of the leptin receptor in diabetic mice," 1996 Nature 379:632–635.
Wang et al., "A novel leptin receptor isoform in rat," 1996 FEBS Letters 392:87–90.
White et al., "Leptin Receptor (OB–R) Signaling," 1997 J. Biol. Chem. 272(7):4065–4071.
J.A. Wells, "Structure and functional basis for hormone binding and receptor oligomerization," 1994 Curr. Opinion in Cell Biol. 6:163–173.
Tartaglia et al., "Identification and Expression Cloning of a Leptin Receptor, OB–R," 1995 Cell 83:1263–1271.

Shields et al., "The Evolution of Haematopoietic Cytokine/Receptor Complexes," 1995 Cytokine 7(7):679–688.
Guan et al., "Differential Expression of mRNA for Leptin Receptor Isoforms in the Rat Brain," 1997 Molec. and Cell Endocrin. 133:1–7.
Murakami et al., "Cloning of Rat Obese cDNA and its Expression in Obese Rats." 1995 Biochem. and Biophs. Res. Comm. 209(3):944–952.
Phillips et al., "Leptin receptor missense mutation in the fatty Zucker rat," 1996 Nature Genetics 13(1):18–19.
Chen et al. "Evidence That the Diabetes Gene Encodes the Leptin Receptor: Identification of a Mutation in the Leptin Receptor Gene in db/db Mice," 1996 Cell 84:491–495.
Chua et al. "Phenotypes of mouse diabetes and rat fatty due to mutations in the OB (leptin) receptor," 1996 Science 271:994–996.
Chua et al. "Phenotype of fatty due to Gln269Pro mutation in the leptin receptor (Lepr)," 1996 Diabetes 45:1141–1143.
Bennett et al., "A role for leptin and its cognate receptor in hematopoiesis," 1996 Current Biology 6(9):1170–1180.
Rosenblum et al. "Functional STAT 1 and signaling by the leptin receptor (OB–R): reduced expression of the rat fatty leptin receptor in transfected cells", 1996 Endocrinology 137:5178–5181.
Spiegelman et al. "Adipogenesis and Obesity: Rounding out the big picture", 1996 Cell 87:377–389.
Stephens et al. "The role of neuropeptide Y in the antiobesity action of the obese gene product", 1995 Nature 377:530–532.
Takaya et al. "Molecular cloning of rat leptin receptor isoform complementary DNAs—identification of a missense mutation in Zucker fatty (fa/fa) rats", 1996 Biochem Biophys Res Comm 225:75–83.
Iida et al., "Phenotype–Linked Amino Acid Alteration in Leptin Receptor cDNA from Zucker Fatty (fa/fa) Rat," 1996 Biochem. and Biophys. Res. Comm. 222:19–26.

* cited by examiner

*Primary Examiner*—Yvonne Eyler
*Assistant Examiner*—Eileen B. O'Hara
(74) *Attorney, Agent, or Firm*—Patricia Chisholm; Anna L. Cocuzzo; Jack L. Tribble (57) ABSTRACT

Mutant ob receptors have been made which a) lack a functional first CK-F3 domain; b) lack a functional second CK-F3 domain or c) lack a functional intracellular domain. These receptors may be used in various assays, such as a transactivation assay to identify novel ligands.

11 Claims, 5 Drawing Sheets

Figure 1

```
    MICQKFCVVL  LHWEFIYVIT  AFNLSYPITP  WRFKLSCMPP  STPRVFTTQD
    VIYFPPKILT  SVGSNVSFHC  IYKKENKIVP  SKEIVWWMNL  AEKIPQSQYD
 5  VVSDHVSKVT  FFNLNETKPR  GKFTYDAVYC  CNEHECHHRY  AELYVIDVNI
    NISCETDGYL  TKMTCRWSTS  TIQSLAESTL  QLRYHRSSLY  CSDIPSIHPI
    SEPKDCYLQS  DGFYECIFQP  IFLLSGYTMW  IRINHSLGSL  DSPPTCVLPD
    SVVKPLPPSS  VKAEITINIG  LLKISWEKPV  FPENNLQFQI  RYGLSGKEVQ
    WKMYEVYDAK  SKSVSLPVPD  LCAVYAVQVR  CKRLDGLGYW  SNWSNPAYTV
10  VMDIKVPMRG  PEFWRIINGD  TMKKEKNVTL  LWKPLMKNDS  LCSVQRYVIN
    HHTSCNGTWS  EDVGNHTKFT  FLWTEQAHTV  TVLAINSIGA  SVANFNLTFS
    WPMSKVNIVQ  SLSAYPLNSS  CVIVSWILSP  SDYKLMYFII  EWKNLNEDGE
    IKWLRISSSV  KKYYIHDHFI  PIEKYQFSLY  PIFMEGVGKP  KIINSFTQDD
    IEKHQSDAGL  YVIVPVIISS  SILLLGTLLI  SHQRMKKLFW  EDVPNPKNCS
15  WAQGLNFQKP  ETFEHLFIKH  TASVTCGPLL  LEPETISEDI  SVDTSWKNKD
    EMMPTTVVSL  LSTTDLEKGS  VCISDQFNSV  NFSEAEGTEV  TYEAESQRQP
    FVKYATLISN  SKPSETGEEQ  GLINSSVTKC  FSSKNSPLKD  SFSNSSWEIE
    AQAFFILSDQ  HPNIISPHLT  FSEGLDELLK  LEGNFPEENN  DKKSIYYLGV
    TSIKKRESGV  LLTDKSRVSC  PFPAPCLFTD  IRVLQDSCSH  FVENNINLGT
20  SSKKTFASYM  PQFQTCSTQT  HKIMENKMCD  LTV
```

Figure 2

```
    MICQKFCVVL LHWEFIYVIT AFNLSYPITP WRFKLSCMPP NSTYDYFLLP
    AGLSKNTSNS NGHYETAVEP KFNSSGTHFS NLSKTTFHCC FRSEQDRNCS
 5  LCADNIEGKT FVSTVNSLVF QQIDANWNIQ CWLKGDLKLF ICYVESLFKN
    LFRNYNYKVH LLYVLPEVLE DSPLVPQKGS FQMVHCNCSV HECCECLVPV
    PTAKLNDTLL MCLKITSGGV IFQSPLMSVQ PINMVKPDPP LGLHMEITDD
    GNLKISWSSP PLVPFPLQYQ VKYSENSTTV IREADKIVSA TSLLVDSILP
    GSSYEVQVRG KRLDGPGIWS DWSTPRVFTT QDVIYFPPKI LTSVGSNVSF
10  HCIYKKENKI VPSKEIVWWM NLAEKIPQSQ YDVVSDHVSK VTFFNLNETK
    PRGKFTYDAV YCCNEHECHF QPIFLLSGYT MWIRINHSLG SLDSPPTCVL
    PDSVVKPLPP SSVKAEITIN IGLLKISWEK PVFPENNLQF QIRYGLSGKE
    VQWKMYEVYD AKSKSVSLPV PDLCAVYAVQ VRCKRLDGLG YWSNWSNPAY
    TVECIFQPIF LLSGYTMWIR INHSLGSLDS PPTCVLPDSV VKPLPPSSVK
15  AEITINIGLL KISWEKPVFP ENNLQFQIRY GLSGKEVQWK MYEVYDAKSK
    SVSLPVPDLC AVYAVQVRCK RLDGLGYWSN WSNPAYTVVM DIKVPMRGPE
    FWRIINGDTM KKEKNVTLLW KPLMKNDSLC SVQRYVINHH TSCNGTWSED
    VGNHTKFTFL WTEQAHTVTV LAINSIGASV ANFNLTFSWP MSKVNIVQSL
    SAYPLNSSCV IVSWILSPSD YKLMYFIIEW KNLNEDGEIK WLRISSSVKK
20  YYIHDHFIPI EKYQFSLYPI FMEGVGKPKI INSFTQDDIE KHQSDAGLYV
    IVPVIISSSI LLLGTLLISH QRMKKLFWED VPNPKNCSWA QGLNFQKPET
    FEHLFIKHTA SVTCGPLLLE PETISEDISV DTSWKNKDEM MPTTVVSLLS
    TTDLEKGSVC ISDQFNSVNF SEAEGTEVTY EAESQRQPFV KYATLISNSK
    PSETGEEQGL INSSVTKCFS SKNSPLKDSF SNSSWEIEAQ AFFILSDQHP
25  NIISPHLTFS EGLDELLKLE GNFPEENNDK KSIYYLGVTS IKKRESGVLL
    TDKSRVSCPF PAPCLFTDIR VLQDSCSHFV ENNINLGTSS KKTFASYMPQ
    FQTCSTQTHK IMENKMCDLT V
```

```
     MICQKFCVVL LHWEFIYVIT AFHRYAELYV IDVNINISCE TDGYLTKMTC
  5  RWSTSTIQSL AESTLQLRYH RSSLYCSDIP SIHPISEPKD CYLQSDGFYE
     CIFQPIFLLS GYTMWIRINH SLGSLDSPPT CVLPDSVVKP LPPSSVKAEI
     TINIGLLKIS WEKPVFPENN LQFQIRYGLS GKEVQWKMYE VYDAKSKSVS
     LPVPDLCAVY AVQVRCKRLD GLGYWSNWSN PAYTV
```

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 883 amino acids
      (B) TYPE: amino acid
      (C) STRANDEDNESS: unknown
      (D) TOPOLOGY: linear    (ii) MOLECULE TYPE: protein    (xi) SEQUENCE DESCRIPTION: SEQ ID NO:1:

```
Met Ile Cys Gln Lys Phe Cys Val Val Leu Leu His Trp Glu Phe Ile
 1               5                  10                  15

Tyr Val Ile Thr Ala Phe Asn Leu Ser Tyr Pro Ile Thr Pro Trp Arg
            20                  25                  30

Phe Lys Leu Ser Cys Met Pro Pro Ser Thr Pro Arg Val Phe Thr Thr
        35                  40                  45

Gln Asp Val Ile Tyr Phe Pro Pro Lys Ile Leu Thr Ser Val Gly Ser
    50                  55                  60

Asn Val Ser Phe His Cys Ile Tyr Lys Lys Glu Asn Lys Ile Val Pro
```

-continued

```
             65                    70                    75                    80
        Ser Lys Glu Ile Val Trp Trp Met Asn Leu Ala Glu Lys Ile Pro Gln
                            85                    90                    95
        Ser Gln Tyr Asp Val Val Ser Asp His Val Ser Lys Val Thr Phe Phe
                           100                   105                   110
        Asn Leu Asn Glu Thr Lys Pro Arg Gly Lys Phe Thr Tyr Asp Ala Val
                           115                   120                   125
        Tyr Cys Cys Asn Glu His Glu Cys His His Arg Tyr Ala Glu Leu Tyr
                           130                   135                   140
        Val Ile Asp Val Asn Ile Asn Ile Ser Cys Glu Thr Asp Gly Tyr Leu
        145                   150                   155                   160
        Thr Lys Met Thr Cys Arg Trp Ser Thr Ser Thr Ile Gln Ser Leu Ala
                           165                   170                   175
        Glu Ser Thr Leu Gln Leu Arg Tyr His Arg Ser Ser Leu Tyr Cys Ser
                           180                   185                   190
        Asp Ile Pro Ser Ile His Pro Ile Ser Glu Pro Lys Asp Cys Tyr Leu
                           195                   200                   205
        Gln Ser Asp Gly Phe Tyr Glu Cys Ile Phe Gln Pro Ile Phe Leu Leu
                           210                   215                   220
        Ser Gly Tyr Thr Met Trp Ile Arg Ile Asn His Ser Leu Gly Ser Leu
        225                   230                   235                   240
        Asp Ser Pro Pro Thr Cys Val Leu Pro Asp Ser Val Val Lys Pro Leu
                           245                   250                   255
        Pro Pro Ser Ser Val Lys Ala Glu Ile Thr Ile Asn Ile Gly Leu Leu
                           260                   265                   270
        Lys Ile Ser Trp Glu Lys Pro Val Phe Pro Glu Asn Asn Leu Gln Phe
                           275                   280                   285
        Gln Ile Arg Tyr Gly Leu Ser Gly Lys Glu Val Gln Trp Lys Met Tyr
                           290                   295                   300
        Glu Val Tyr Asp Ala Lys Ser Lys Ser Val Ser Leu Pro Val Pro Asp
        305                   310                   315                   320
        Leu Cys Ala Val Tyr Ala Val Gln Val Arg Cys Lys Arg Leu Asp Gly
                           325                   330                   335
        Leu Gly Tyr Trp Ser Asn Trp Ser Asn Pro Ala Tyr Thr Val Val Met
                           340                   345                   350
        Asp Ile Lys Val Pro Met Arg Gly Pro Glu Phe Trp Arg Ile Ile Asn
                           355                   360                   365
        Gly Asp Thr Met Lys Lys Glu Lys Asn Val Thr Leu Leu Trp Lys Pro
                           370                   375                   380
        Leu Met Lys Asn Asp Ser Leu Cys Ser Val Gln Arg Tyr Val Ile Asn
        385                   390                   395                   400
        His His Thr Ser Cys Asn Gly Thr Trp Ser Glu Asp Val Gly Asn His
                           405                   410                   415
        Thr Lys Phe Thr Phe Leu Trp Thr Glu Gln Ala His Thr Val Thr Val
                           420                   425                   430
        Leu Ala Ile Asn Ser Ile Gly Ala Ser Val Ala Asn Phe Asn Leu Thr
                           435                   440                   445
        Phe Ser Trp Pro Met Ser Lys Val Asn Ile Val Gln Ser Leu Ser Ala
                           450                   455                   460
        Tyr Pro Leu Asn Ser Ser Cys Val Ile Val Ser Trp Ile Leu Ser Pro
        465                   470                   475                   480
        Ser Asp Tyr Lys Leu Met Tyr Phe Ile Ile Glu Trp Lys Asn Leu Asn
                           485                   490                   495
```

```
Glu Asp Gly Glu Ile Lys Trp Leu Arg Ile Ser Ser Val Lys Lys
            500                 505                 510

Tyr Tyr Ile His Asp His Phe Ile Pro Ile Glu Lys Tyr Gln Phe Ser
            515                 520                 525

Leu Tyr Pro Ile Phe Met Glu Gly Val Gly Lys Pro Lys Ile Ile Asn
            530                 535             540

Ser Phe Thr Gln Asp Ile Glu Lys His Gln Ser Asp Ala Gly Leu
545                 550                 555                 560

Tyr Val Ile Val Pro Val Ile Ile Ser Ser Ile Leu Leu Leu Gly
                565                 570                 575

Thr Leu Leu Ile Ser His Gln Arg Met Lys Lys Leu Phe Trp Glu Asp
            580                 585                 590

Val Pro Asn Pro Lys Asn Cys Ser Trp Ala Gln Gly Leu Asn Phe Gln
            595                 600                 605

Lys Pro Glu Thr Phe Glu His Leu Phe Ile Lys His Thr Ala Ser Val
            610                 615                 620

Thr Cys Gly Pro Leu Leu Leu Glu Pro Glu Thr Ile Ser Glu Asp Ile
625                 630                 635                 640

Ser Val Asp Thr Ser Trp Lys Asn Lys Asp Glu Met Met Pro Thr Thr
                645                 650                 655

Val Val Ser Leu Leu Ser Thr Thr Asp Leu Glu Lys Gly Ser Val Cys
                660                 665                 670

Ile Ser Asp Gln Phe Asn Ser Val Asn Phe Ser Glu Ala Glu Gly Thr
            675                 680                 685

Glu Val Thr Tyr Glu Ala Glu Ser Gln Arg Gln Pro Phe Val Lys Tyr
            690                 695                 700

Ala Thr Leu Ile Ser Asn Ser Lys Pro Ser Glu Thr Gly Glu Glu Gln
705                 710                 715                 720

Gly Leu Ile Asn Ser Ser Val Thr Lys Cys Phe Ser Ser Lys Asn Ser
                725                 730                 735

Pro Leu Lys Asp Ser Phe Ser Asn Ser Ser Trp Glu Ile Glu Ala Gln
            740                 745                 750

Ala Phe Phe Ile Leu Ser Asp Gln His Pro Asn Ile Ile Ser Pro His
            755                 760                 765

Leu Thr Phe Ser Glu Gly Leu Asp Glu Leu Leu Lys Leu Glu Gly Asn
770                 775                 780

Phe Pro Glu Glu Asn Asn Asp Lys Lys Ser Ile Tyr Tyr Leu Gly Val
785                 790                 795                 800

Thr Ser Ile Lys Lys Arg Glu Ser Gly Val Leu Leu Thr Asp Lys Ser
            805                 810                 815

Arg Val Ser Cys Pro Phe Pro Ala Pro Cys Leu Phe Thr Asp Ile Arg
            820                 825                 830

Val Leu Gln Asp Ser Cys Ser His Phe Val Glu Asn Asn Ile Asn Leu
            835                 840                 845

Gly Thr Ser Ser Lys Lys Thr Phe Ala Ser Tyr Met Pro Gln Phe Gln
            850                 855                 860

Thr Cys Ser Thr Gln Thr His Lys Ile Met Glu Asn Lys Met Cys Asp
865                 870                 875                 880

Leu Thr Val
```

(2) INFORMATION FOR SEQ ID NO:2:

(i) SEQUENCE CHARACTERISTICS:

(A) LENGTH: 1221 amino acids
(B) TYPE: amino acid
(C) STRANDEDNESS: unknown
(D) TOPOLOGY: linear (ii) MOLECULE TYPE: protein (xi) SEQUENCE DESCRIPTION: SEQ ID NO:2:

```
Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
            35                  40                  45

Leu Pro Ala Gly Leu Ser Lys Asn Thr Ser Asn Ser Asn Gly His Tyr
        50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
            115                 120                 125

Ile Gln Cys Trp Leu Lys Gly Asp Leu Lys Leu Phe Ile Cys Tyr Val
        130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
            275                 280                 285

Ser Ala Thr Ser Leu Leu Val Asp Ser Ile Leu Pro Gly Ser Ser Tyr
        290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
        355                 360                 365

Trp Met Asn Leu Ala Glu Lys Ile Pro Gln Ser Gln Tyr Asp Val Val
```

-continued

```
            370                 375                 380
Ser Asp His Val Ser Lys Val Thr Phe Phe Asn Leu Asn Glu Thr Lys
385                 390                 395                 400
Pro Arg Gly Lys Phe Thr Tyr Asp Ala Val Tyr Cys Cys Asn Glu His
                    405                 410                 415
Glu Cys His Phe Gln Pro Ile Phe Leu Leu Ser Gly Tyr Thr Met Trp
                420                 425                 430
Ile Arg Ile Asn His Ser Leu Gly Ser Leu Asp Ser Pro Pro Thr Cys
            435                 440                 445
Val Leu Pro Asp Ser Val Val Lys Pro Leu Pro Pro Ser Ser Val Lys
    450                 455                 460
Ala Glu Ile Thr Ile Asn Ile Gly Leu Leu Lys Ile Ser Trp Glu Lys
465                 470                 475                 480
Pro Val Phe Pro Glu Asn Asn Leu Gln Phe Gln Ile Arg Tyr Gly Leu
                    485                 490                 495
Ser Gly Lys Glu Val Gln Trp Lys Met Tyr Glu Val Tyr Asp Ala Lys
                500                 505                 510
Ser Lys Ser Val Ser Leu Pro Val Pro Asp Leu Cys Ala Val Tyr Ala
            515                 520                 525
Val Gln Val Arg Cys Lys Arg Leu Asp Gly Leu Gly Tyr Trp Ser Asn
    530                 535                 540
Trp Ser Asn Pro Ala Tyr Thr Val Glu Cys Ile Phe Gln Pro Ile Phe
545                 550                 555                 560
Leu Leu Ser Gly Tyr Thr Met Trp Ile Arg Ile Asn His Ser Leu Gly
                    565                 570                 575
Ser Leu Asp Ser Pro Pro Thr Cys Val Leu Pro Asp Ser Val Val Lys
                580                 585                 590
Pro Leu Pro Pro Ser Ser Val Lys Ala Glu Ile Thr Ile Asn Ile Gly
            595                 600                 605
Leu Leu Lys Ile Ser Trp Glu Lys Pro Val Phe Pro Glu Asn Asn Leu
    610                 615                 620
Gln Phe Gln Ile Arg Tyr Gly Leu Ser Gly Lys Glu Val Gln Trp Lys
625                 630                 635                 640
Met Tyr Glu Val Tyr Asp Ala Lys Ser Lys Ser Val Ser Leu Pro Val
                    645                 650                 655
Pro Asp Leu Cys Ala Val Tyr Ala Val Gln Val Arg Cys Lys Arg Leu
                660                 665                 670
Asp Gly Leu Gly Tyr Trp Ser Asn Trp Ser Asn Pro Ala Tyr Thr Val
            675                 680                 685
Val Met Asp Ile Lys Val Pro Met Arg Gly Pro Glu Phe Trp Arg Ile
    690                 695                 700
Ile Asn Gly Asp Thr Met Lys Lys Glu Lys Asn Val Thr Leu Leu Trp
705                 710                 715                 720
Lys Pro Leu Met Lys Asn Asp Ser Leu Cys Ser Val Gln Arg Tyr Val
                    725                 730                 735
Ile Asn His His Thr Ser Cys Asn Gly Thr Trp Ser Glu Asp Val Gly
                740                 745                 750
Asn His Thr Lys Phe Thr Phe Leu Trp Thr Glu Gln Ala His Thr Val
            755                 760                 765
Thr Val Leu Ala Ile Asn Ser Ile Gly Ala Ser Val Ala Asn Phe Asn
    770                 775                 780
Leu Thr Phe Ser Trp Pro Met Ser Lys Val Asn Ile Val Gln Ser Leu
785                 790                 795                 800
```

-continued

Ser Ala Tyr Pro Leu Asn Ser Ser Cys Val Ile Val Ser Trp Ile Leu
            805                 810                 815

Ser Pro Ser Asp Tyr Lys Leu Met Tyr Phe Ile Ile Glu Trp Lys Asn
            820                 825                 830

Leu Asn Glu Asp Gly Glu Ile Lys Trp Leu Arg Ile Ser Ser Ser Val
            835                 840                 845

Lys Lys Tyr Tyr Ile His Asp His Phe Ile Pro Ile Glu Lys Tyr Gln
            850                 855                 860

Phe Ser Leu Tyr Pro Ile Phe Met Glu Gly Val Gly Lys Pro Lys Ile
865                 870                 875                 880

Ile Asn Ser Phe Thr Gln Asp Ile Glu Lys His Gln Ser Asp Ala
            885                 890                 895

Gly Leu Tyr Val Ile Val Pro Val Ile Ile Ser Ser Ile Leu Leu
            900                 905                 910

Leu Gly Thr Leu Leu Ile Ser His Gln Arg Met Lys Lys Leu Phe Trp
            915                 920                 925

Glu Asp Val Pro Asn Pro Lys Asn Cys Ser Trp Ala Gln Gly Leu Asn
            930                 935                 940

Phe Gln Lys Pro Glu Thr Phe Glu His Leu Phe Ile Lys His Thr Ala
945                 950                 955                 960

Ser Val Thr Cys Gly Pro Leu Leu Leu Glu Pro Glu Thr Ile Ser Glu
            965                 970                 975

Asp Ile Ser Val Asp Thr Ser Trp Lys Asn Lys Asp Glu Met Met Pro
            980                 985                 990

Thr Thr Val Val Ser Leu Leu Ser Thr Thr Asp Leu Glu Lys Gly Ser
            995                 1000                1005

Val Cys Ile Ser Asp Gln Phe Asn Ser Val Asn Phe Ser Glu Ala Glu
            1010                1015                1020

Gly Thr Glu Val Thr Tyr Glu Ala Glu Ser Gln Arg Gln Pro Phe Val
1025                1030                1035                1040

Lys Tyr Ala Thr Leu Ile Ser Asn Ser Lys Pro Ser Glu Thr Gly Glu
            1045                1050                1055

Glu Gln Gly Leu Ile Asn Ser Ser Val Thr Lys Cys Phe Ser Ser Lys
            1060                1065                1070

Asn Ser Pro Leu Lys Asp Ser Phe Ser Asn Ser Ser Trp Glu Ile Glu
            1075                1080                1085

Ala Gln Ala Phe Phe Ile Leu Ser Asp Gln His Pro Asn Ile Ile Ser
            1090                1095                1100

Pro His Leu Thr Phe Ser Glu Gly Leu Asp Glu Leu Leu Lys Leu Glu
1105                1110                1115                1120

Gly Asn Phe Pro Glu Glu Asn Asn Asp Lys Lys Ser Ile Tyr Tyr Leu
            1125                1130                1135

Gly Val Thr Ser Ile Lys Lys Arg Glu Ser Gly Val Leu Leu Thr Asp
            1140                1145                1150

Lys Ser Arg Val Ser Cys Pro Phe Pro Ala Pro Cys Leu Phe Thr Asp
            1155                1160                1165

Ile Arg Val Leu Gln Asp Ser Cys Ser His Phe Val Glu Asn Asn Ile
            1170                1175                1180

Asn Leu Gly Thr Ser Ser Lys Lys Thr Phe Ala Ser Tyr Met Pro Gln
1185                1190                1195                1200

Phe Gln Thr Cys Ser Thr Gln Thr His Lys Ile Met Glu Asn Lys Met
            1205                1210                1215

```
Cys Asp Leu Thr Val
        1220

(2) INFORMATION FOR SEQ ID NO:3:

(i) SEQUENCE CHARACTERISTICS:
        (A) LENGTH: 235 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:3:

Met Ile Cys Gln Lys Phe Cys Val Val Leu Leu His Trp Glu Phe Ile
1               5                   10                  15

Tyr Val Ile Thr Ala Phe His Arg Tyr Ala Glu Leu Tyr Val Ile Asp
            20                  25                  30

Val Asn Ile Asn Ile Ser Cys Glu Thr Asp Gly Tyr Leu Thr Lys Met
        35                  40                  45

Thr Cys Arg Trp Ser Thr Ser Thr Ile Gln Ser Leu Ala Glu Ser Thr
    50                  55                  60

Leu Gln Leu Arg Tyr His Arg Ser Ser Leu Tyr Cys Ser Asp Ile Pro
65                  70                  75                  80

Ser Ile His Pro Ile Ser Glu Pro Lys Asp Cys Tyr Leu Gln Ser Asp
                85                  90                  95

Gly Phe Tyr Glu Cys Ile Phe Gln Pro Ile Phe Leu Leu Ser Gly Tyr
                100                 105                 110

Thr Met Trp Ile Arg Ile Asn His Ser Leu Gly Ser Leu Asp Ser Pro
            115                 120                 125

Pro Thr Cys Val Leu Pro Asp Ser Val Val Lys Pro Leu Pro Pro Ser
        130                 135                 140

Ser Val Lys Ala Glu Ile Thr Ile Asn Ile Gly Leu Leu Lys Ile Ser
145                 150                 155                 160

Trp Glu Lys Pro Val Phe Pro Glu Asn Asn Leu Gln Phe Gln Ile Arg
                165                 170                 175

Tyr Gly Leu Ser Gly Lys Glu Val Gln Trp Lys Met Tyr Glu Val Tyr
            180                 185                 190

Asp Ala Lys Ser Lys Ser Val Ser Leu Pro Val Pro Asp Leu Cys Ala
        195                 200                 205

Val Tyr Ala Val Gln Val Arg Cys Lys Arg Leu Asp Gly Leu Gly Tyr
    210                 215                 220

Trp Ser Asn Trp Ser Asn Pro Ala Tyr Thr Val
225                 230                 235

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "leptin response element"

(xi) SEQUENCE DESCRIPTION: SEQ ID NO:4:

CTGATTTCCC CGAAATGACG                                          20

(2) INFORMATION FOR SEQ ID NO:5:
```

(i) SEQUENCE CHARACTERISTICS:
    (A) LENGTH: 9 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "oligonucleotide"

(xi) SEQUENCE DESCRIPTION: SEQ ID NO:5:

CCACCAAGT      9

(2) INFORMATION FOR SEQ ID NO:6:

(i) SEQUENCE CHARACTERISTICS:
        (A) LENGTH: 13 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "oligonucleotide"

(xi) SEQUENCE DESCRIPTION: SEQ ID NO:6:

ACTTGGTGGC ATG      13

(2) INFORMATION FOR SEQ ID NO:7:

(i) SEQUENCE CHARACTERISTICS:
        (A) LENGTH: 38 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "oligonucleotide"

(xi) SEQUENCE DESCRIPTION: SEQ ID NO:7:

GAACATGAAT GCCATTTCCA GCCAATCTTC CTATTATC      38

(2) INFORMATION FOR SEQ ID NO:8:

(i) SEQUENCE CHARACTERISTICS:
        (A) LENGTH: 35 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "oligonucleotide"

(xi) SEQUENCE DESCRIPTION: SEQ ID NO:8:

GGAAAATGCA TTCAACTGTG TAGGCTGGAT TGCTC      35

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "oligonucleotide"

(xi) SEQUENCE DESCRIPTION: SEQ ID NO:9:

TTCCAGCCAA TCTTCCTATT ATC      23

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "oligonucleotide"

(xi) SEQUENCE DESCRIPTION: SEQ ID NO:10:

```
GACATCTCTA GACATTCTTT GGTGTGATAT TAATAATG                          38
```

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "oligonucleotide"

(xi) SEQUENCE DESCRIPTION: SEQ ID NO:11:

```
CTGATTTCCC CGAATGACG                                               19
```

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: other nucleic acid
        (A) DESCRIPTION: /desc = "oligonucleotide"

(xi) SEQUENCE DESCRIPTION: SEQ ID NO:12:

```
CGTCATTTCG GGGAAATCAT                                              20
```

US 6,632,625 B1

MUTANT OB RECEPTORS AND NUCLEOTIDES ENCODING THEM

CROSS-REFERENCE TO RELATED APPLICATIONS

The instant application claims priority under 35 U.S.C. §119(e) to U.S. provisional application serial No. 60/032,367 filed Dec. 2, 1996, now abandoned.

STATEMENT REGARDING FEDERALLY-SPONSORED R&D

Not Applicable.

REFERENCE TO MICROFICHE APPENDIX

Not Applicable.

FIELD OF THE INVENTION

This invention relates to mutant ob receptor proteins, to nucleotides encoding them, and to assays using the mutant receptor proteins.

BACKGROUND OF THE INVENTION

Recently the identification of mutations in several genes involved in the onset of obesity in rodents have been identified. Of particular interest are mutations discovered in the peptide hormone, leptin, which is a component of a novel signal transduction pathway that regulates body weight (Zhang et al. 1994, *Nature* 372:425–432; Chen et al. 1996, *Cell* 84:491–495). Leptin was initially discovered by the positional cloning of the obesity gene, ob, in mice. Two different ob alleles have been identified: one mutation causes the premature termination of the leptin peptide resulting in a truncated protein, and the other mutation changes the transcriptional activity of the obesity (ob) gene, resulting in a reduced amount of circulating leptin.

There is a correlation between a decrease in the levels of biologically active leptin and the overt obese phenotype observed in ob/ob mice. Recombinant leptin has been shown to induce weight loss in the ob/ob mouse but not in the diabetic phenotype db/db mouse (Campfield et al. 1995, *Science* 269: 546–549; Halaas et al. 1995, *Science* 269: 543–546; Pellymounter et al. 1995, *Science* 269:540–543; Rentsch et al. 1995, *Biochem. Biophys. Res. Comm.* 214:131–136; and Weigle et al. 1995, *J. Clin. Invest.* 96:2065–2070).

Although the synthesis of leptin occurs in the adipocyte, its ability to decrease food intake and increase metabolic rate appears to be mediated centrally by the hypothalamus. Injection of recombinant leptin into the third ventricle of the brain elicits a similar response as peripheral administration of leptin. Furthermore, the recent cloning of the human receptor for the leptin, the ob-receptor (OB-R), reveals that it is transcribed in the hypothalamus (Tartaglia et al. 1995, *Cell* 83:1263–1271; Stephens et al. 1995, *Nature* 377: 530–532). In addition, a mutation that results in premature termination of the long-form of the mouse OB-R, which is preferentially expressed in the hypothalamus, appears to be responsible for the obese phenotype of the db/db mouse (Lee et al. 1996, *Nature* 379:632–635; Chua et al. 1996, *Science* 271:994–996; and Chen et al. 1996, *Cell* 84:491–495).

It would be desirable to clone and produce mutant ob receptor proteins to use in assays for the identification of ligands which may be useful in understanding obesity and for its prevention and treatment.

SUMMARY OF THE INVENTION

Not Applicable.

BRIEF DESCRIPTION OF THE DRAWINGS

Not Applicable.

DETAILED DESCRIPTION OF THE INVENTION

This invention relates to mutant ob receptors ("OB-Rs"), also referred to as "leptin receptors" which differ from wild type receptors by having a mutation selected from the group consisting of:

a) lacking a functional first CK-F3 module;
b) lacking a functional second CK-F3 module; and
c) lacking a functional intracellular domain.

The expression "lack a functional" module or domain means that the receptor no longer has biological function associated with structural portion of the receptor molecule. This may be accomplished by deletion of the module or domain, or by substitutions the amino acids which make up one domain by other amino acids such that function is lost.

This invention also relates to mutant ob receptors, which are selected from the group consisting of:

a) receptors which contain a deletion of amino acid residues which comprise all or substantially all of the first CK-F3 module;
b) receptors which contain a substitution of all or substantially all of a F3 domain for a CK domain in a second CK-F3 module, resulting in a F3-F3 module; and
c) receptors which have a deletion of all or substantially all of the intracellular domain.

Another aspect of this invention is to nucleic acids which encode a mutant OB-R of this invention. Preferably, the nucleic acid is DNA.

This invention also includes vectors containing a mutant OB-R gene, host cells containing the vectors, and methods of making mutant OB-R protein comprising the steps of introducing a vector comprising a mutant OB-R gene into a host cell, and cultivating the host cell under appropriate conditions such that mutant OB-R is produced. The mutant OB-R so produced may be harvested from the host cells in conventional ways.

Yet another aspect of this invention are assays which employ a mutant OB-R. In these assays, various molecules, suspected of being wild-type OB-R ligands are contacted with a mutant OB-R, and their binding is detected. A particularly preferred type of assay is a transactivation assay, wherein the binding of the ligand to a mutant OB-R initiates a cascade of intracellular events, resulting in transcription and/or translation of a reporter gene which can be detected. Using the assays of this invention, agonists, antagonists, and ligand mimetics may be identified. A further aspect of this invention are the ligands so indentified.

Still another aspect of this invention is the use of the mutant receptors of this invention in gene therapy. Genes encoding the mutant receptors may be transferred into an animal in need of treatment, and the regulation of weight gain may be influenced.

As used througout the specification and claims, the following definitions apply:

"Wild type" means that the gene or protein is substantially the same as that found in the reference species, and which is not considered to have a mutation for that gene or protein. "Substantially the same" when referreing to a nucleic acid or amino acid sequence means either it is the same as the reference sequence, or if not exactly the same, contains changes which do not affect its biological activity or function.

"Substantially all" when referring to a deletion means that the deletion is extensive enough so that the particular domain or module no longer retains its biological function.

The OB-R is a member of the cytokine receptor family. The cytokine receptor family is a relatively large family and includes: Growth Hormone Receptor (GH-R), Erythropoietin Receptor (EPO-R) and Granulocyte Colony Stimulating Fator (GCSF-R).

GH-R is one of two receptors for which high resolution structure is currently available. The extracellular region of the GH-R is composed of two domains, a CK domain and a F3 domain, both of which are characterized by unique consensus residues. The combined CK-F3 module forms the growth hormone binding site.

Sequence alignment between the OB-R and the GH-R reveals that the extracellular region of the OB-R contains two homologous units of the CK-F3 module. The first CK-F3 module extends from amino acids 41–326. Its CK domain extends from amino acid 41 to 222, and its F3 domain is from amino acid 223 to 326. The second CK-F3 module extends from amino acids 431–632. Its CK domain is from amino acids 431 to 508 and its F3 domain is from amino acids 509 to 632. The repeating CK-F3 module motif which is present in the OB-R is not commonly found in cytokine receptors, and the localization of the ligand binding site for those cytokine receptors with repeating CK-F3 modules is not known.

This specification refers to particular amino acids and domains by reference to the human OB-R. However, it is understood that OB-R from other species may be similarly modified to obtain equivalent mutants of those described specifically herein, and the invention is not limited to mutations of the human OB-R.

In accordance with this invention, three classes of leptin receptor mutants were constructed. The first class lacks a functional first CK-F3 module.

One embodiment of this class is a deletion mutant wherein all or substantially all of the first CK-F3 module and, preferably, the region of the first CK-F3 module extending from amino acids 41 to 326, has been deleted.

In one preferred embodiment of this invention, the entire first CK-F3 module has been deleted. This particular mutant was designated D(41–322). Surprisingly, D(41–322) binds recombinant leptin with the same affinity as the wild type receptor (IC50=0.5 nM), and in the transactivation assay of this invention (described more fully below) it is functionally active in inducing the synthesis of luciferase (EC50=0.2 nM). This finding is unexpected since point mutations and deletions in the N-terminal domain of the GCSF receptor (which is in the same class of cytokine receptors as OB-R) was shown to negatively affect activity (see Fukunaga et al., 1991 EMBO J. 10:2855–2865). In contrast, the OB-R mutant carrying a deletion in this domain retained activity.

Analyses of the mutants of this invention indicates that one third of the extracellular region of the leptin receptor is not required for binding or activation. The leptin binding site lies within residues 420–632. Using the D(41–322) deletion mutant for compound screening can be advantageous over the wild type because a small molecule compound may bind to both of the CK-F3 modules in the wild type receptor and therefore may complicate data interpretation in the process of establishing a structure-activity relationship for synthetic compounds.

A second class of mutants according to this invention lacks a functional second CK-F3 domain. One embodiment of this class are termed substitution mutants. In a substitution mutant, all or substantially all of the CK domain in the second CK-F3 module (which extends from amino acids 420–496) are removed and replaced with amino acids comprising all or substantially all of the F3 domain in the second CK-F3 module (amino acids 500–632). This results in a new module, F3-F3 which replaces the second CK-F3 module.

In a preferred embodiment, the entire CK domain is replaced with an entire F3 domain in the second module. This mutant was designated (420–496)TO(500–632). This mutant exhibits no detectable level of radiolabeled leptin binding at 0.2 nM, and it is incapable of inducing the synthesis of luciferase in a transactivation assay with up to 100 nM of leptin. This mutant behaves as a dominant negative mutant of the wild-type OB-R. When the latter mutant was coexpressed with the wild-type OB-R, leptin binding or activation was undetectable, suggesting a homodimerization interaction between the subunits. In contrast, coexpression of the deletion (41–322 mutant) retained wildtype activity.

A third class of mutants according to this invention lacks a functional intracellular domain. One group of these mutants contain a deletion of all or substantially all of the intracellular residues (867–1165). A preferred embodiment of this class of mutants has the entire intracellular region deleted. This mutant, D(867–1165), exhibits the same leptin binding affinity as the wild type receptor and yet it is incapable of inducing the synthesis of luciferase in a transactivation assay with up to 100 nM of leptin. This mutant also behaves as a dominant negative mutant of OB-R.

Figure 4:
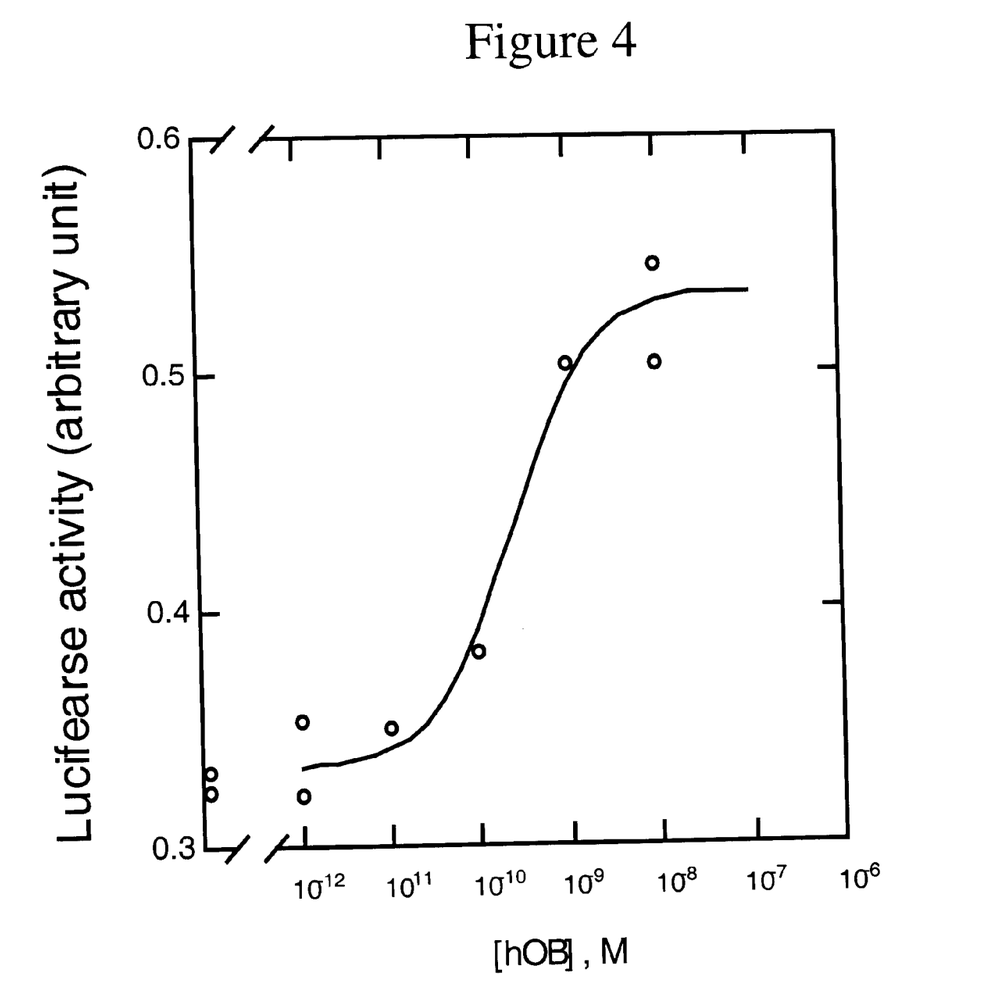
FIG. 4 is a graph of a transactivation assay using the deletion mutant receptor of FIG. 1.
Figure 5:
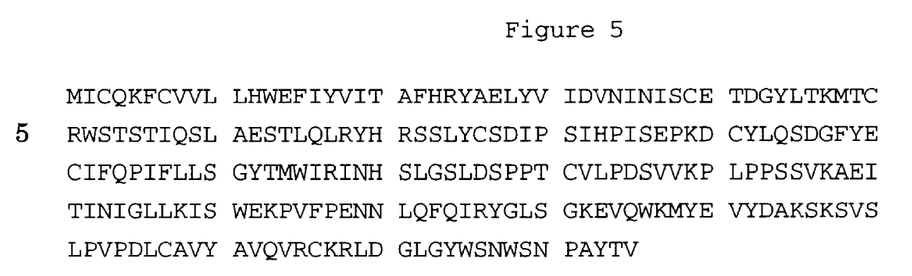
FIG. 5 is the amino acid sequence of the soluble leptin binding domain containing amino acids 1–22 of the leptin receptor as the signal sequence and residues 420–632 of the leptin receptor (SEQ.ID.NO:3).

This invention also relates to a soluble secreted form of leptin binding domain comprised of a secretion signal sequence (residues 1–22) and residues 420–632 of the OB-R (FIG. 4). This leptin bonding domain can be produced by COS or other cells and subsequently purified. Using such a purified soluble binding domain in the screening of OB-R ligands can substantially increase the specificity of the screening assay compared to a cell based assay.

Another aspect of this invention is a transactivation assay which uses the mutant OB-R receptors described above. Transactivation assays which involve membrane-bound receptors have been described in the art. Generally, when a ligand binds to a membrane-bound receptor, a cascade of intracellular events is initiated, ultimately resulting in the binding of a molecule to a portion of a DNA sequence known as the response element. This in turn, initiates transcription of the gene associated with the response element. In a transactivation assay, a reporter construct which contains a reporter gene (such as luciferase or CAT) is placed under the transcriptional control of a response element and introduced into a host cell. The host cell also expresses the receptor of interest (either endogenously or through recombinant expression). When a ligand binds to the receptor, various intracellular signals are generated and ultimately, the reporter gene is transcribed and/or translated. The transcription and/or translation may be detected and measured by a variety of methods, and may even be quantified.

Co-pending U.S. provisional patent applications Serial Nos. 60/016,051, filed Apr. 22, 1996, and 60/031,002, filed Nov. 15, 1996, both of which are hereby incorporated by reference describe transactivation assays for various native OB-Rs.

A further aspect of this invention is a method for determining whether an OB-R ligand is present in a sample comprising.
  a) contacting a cell with the sample wherein the cell expresses a mutant OB-R selected from the group consisting of receptors which lack a functional first CK-F3 module; and
  b) determining if transcription or translation of the reporter gene occurs.

Another aspect of this invention is a method for determining whether an OB-R ligand is present in a sample comprising:
  a) contacting a cell with the sample, wherein the cell expresses an OB-R mutant selected from the group consisting of:
    receptors which contain a deletion of amino acid residues which comprise all or substantially all of a first CK-F3 module;
    wherein the cell also comprises a reporter gene construct, wherein the reporter gene construct comprises a leptin response element operatively linked to a reporter gene; and
  b) determining if transcription or translation of the reporter gene occurs.

In preferred embodiments of this assay, the cell which expresses the mutant receptor does not express endogenous OB-R, or alternatively only expresses a small amount of endogenous receptor. Thus, the amount of transcription and/or translation of the reporter gene will be directly correlated to the binding and activation of the mutant receptor.

The reporter gene construct contains a promoter region which includes a leptin response element, and a reporter gene.

A leptin response element which may be used in accordance with this invention is an IRF-1 derived gamma-interferon activation sequence. IRF-1 derived activation sequences have been described in the art (Pine et al., 1994 *EMBO J.* 13:158–167).

A promoter region is constructed which contains a promoter of choice and one or more leptin response elements. The promoter region may be a hybrid promoter region, i.e. contain a promoter and one or more response elements which do not naturally occur together, or it may be a naturally occurring promoter region with one or more associated response elements. In a preferred embodiment the promoter is a well-characterized promoter, such as the herpes simplex virus thymidine kinase promoter, but any promoter which is known to function in the host cell chosen may be used. It is also preferred that the promoter be a minimal promoter, so that there are no transcriptional control sequences which may influence the activity of the leptin response element(s).

The leptin-response element is preferably placed proximal to the promoter. Intervening sequences may be present between the leptin response element and the promoter, provided they do not interfere with the functioning of the leptin response element.

In accordance with this invention, a suitable leptin response element is an IRF-1 derived gamma interferon activation sequence 5'-CTGATTTCCC CGAAATGACG-3' (SEQ.ID.NO.4). In a preferred embodiment, the promoter region comprises a plurality of IRF-1 derived gamma interferon activation sequences; and more preferably it comprises at least three such sequences. When a plurality of leptin response elements are present, they are preferably joined in tandem. However, there may be interviewing sequences present provided they do not interfere with the functioning of the leptin response elements.

Other cytokine activation sequences, known in the art may also be used in place of or in addition to the IRF-1 derived gamma interferon activation sequence. These include the STAT binding sequences.

In order to detect transcription which occurs as a result of the leptin-OB-R binding, it is preferred to operatively link a reporter gene to the promoter region which contains at least one leptin response element. A reporter gene may be any gene which encodes a peptide which is easily detected, or otherwise allows for easy detection of transcription or translation. It generally encodes a protein which does naturally occur in the host cell or only is produced in small amounts by the host cell. Examples of well known reporter genes include: chloramphenicol acetyl transferase (CAT), green fluorescent protein (GFP), luciferase (either bacterial or firefly), and other enzyme-based detection systems such as β-galactosidase, alkaline phosphatase, and the like. In a particularly preferred embodiment, luciferase is a reporter gene. In alternative embodiments, the mRNA transcribed from the reporter gene DNA may be measured rather than the translation product.

The reporter gene construct, which comprises a) a promoter region which comprises a promoter and at least one leptin response element and b) the reporter gene (operatively linked to the promoter region) is preferably placed in an appropriate vector and in used to transfect a host cell. The vector may be any known vector, including plasmids, cosmids and viral vectors which can function in a chosen host cell.

The host cell may be any cell or cell line which is conveniently cultured. In general, a preferred host cell will be eukaryotic, preferably mammalian, and in particularly preferred embodiments it is a mouse hypothalamic cell (such as GT1–7, NLT or Gn11), a mammalian neuroblastoma cell line, human brain neuron (SK-NMC or SK-N-BE2) mouse fibroblast cell lines such as NIH/3T3 (ATCC CRL 1658) or L (ATCC CCL 1), Chinese hamster ovary CHO-K1 cells (ATCC CCL 61) human embryonic kidney-derived 293 cells (ATCC CRL 1573), or CDS cells.

Another aspect of this invention is an assay to determine if a putative OB-R ligand is present in a sample comprising
  i) contacting a mutant OB-R with the putative ligand wherein the mutant OB-R differ from a wild type receptor by having a mutation selected from the group consisting of:
    a) lacking a functional first CK-F3 module;
    b) lacking a functional CK-F3 module and
    c) lacking a functional intracellular domain; and
  ii) determining if binding occurs.

Determination of binding may be done by any conventional method, including by sue of radiolabeled ligand. One preferred assay compares the amount of binding of radiolabeled leptin which occurs in the presence and absence of the putative ligand. The amount of binding of the putative ligand is related to the inhibition of labeled leptin binding.

Another aspect of this invention is a set of vectors suitable for transfecting a host cell so that it can be used in the assays of this invention. The set of vectors comprises a first vector which contains a mutant OB-R construct. The OB-R construct includes nucleic acids encoding a desired mutated form of the receptor. It may be under the control of its native promoter or any other desired heterologous promoter. Optionally it may also contain other expression-control elements, such as enhancers and sequences which assist in expressing the receptor on the membrane.

The set of vectors also comprises a second vector comprising the reporter gene construct described previously.

In a preferred assay of this invention, compounds which are suspected of being leptin receptor ligands can be assayed. In this embodiment, cells which express a mutant OB-R are transfected with the reporter gene construct described previously. The putative OB-R ligand is placed in contact with the transfected cells, and the presence of the reporter gene transcription or translation product is detected. This may be compared to the amount of transcription or translation measured in a control assay, where an identically transfected cell is placed in contact with leptin. A further advantage of the assay of this invention is that it is dose-dependent; i.e. as more leptin ligand-OB-R binding occurs, transcription and/or translation of reporter gene increases, and therefore allows for a quantitative determination of OB-R binding activity.

A counterscreen may also be employed as a part of this assay. In the counterscreen, a second cell of the same cell type is transfected with the reporter gene construct described previously, but is not transfected with the OB-R gene construct. The putative OB-R ligand is placed in contact with the transfected cells and the presence of of the reporter gene transcription or translation is detected. Those putative OB-R ligands which activate the reporter gene construct only in the presence of leptin receptor are determined to be specific leptin agonists.

Using this embodiment of the assay, leptin agonists and antagonists may be identified. A leptin agonist is a compound which binds to the OB-R, such as a leptin mimetic, and produces a cellular response which is at least about equivalent to that of leptin, and which may be greater than that of leptin. Such compounds would be useful in situations where leptin insufficiency causes obesity, diabetes or infertility.

Also using this embodiment of the assay, leptin antagonists may be identified. A leptin antagonist is a compound which can bind to the OB-R, but produces a lesser response than that of native leptin. Such compounds would be useful in the treatment of anorexia and cachexia.

The mutant leptin receptors of this invention are also useful in gene therapy for weight control. For example, the first class of receptor mutants described (containing a deletion of all or substantially all of the first CK-F3 module) can be transferred to an animal which suffers from obesity due to an insufficient amount of OB-R receptors or which has OB-R receptors which do not function as efficiently as wild-type receptors.

The following non-limiting Examples are presented to better illustrate the invention.

EXAMPLE 1
Receptor Mutant Construction

The deletion mutant of the human OB-R, designated as D(41–322), was constructed as follows. The full length cDNA encoding the wild type human leptin receptor was inserted into the plasmid pcDNA3 (Invitrogen, San Diego, Calif.). The plasmid was cleaved by restriction enzymes SphI at residue 38 and ScaI at residue 324, and the nucleic acids encoding residues 39–323 were removed by gel purification. An adapter was generated by annealing two oligonucleotides (5'-CCACCAAGT (SEQ.ID.NO:5) and 5'-ACTTGGTGGCATG (SEQ.ID.NO:6), and the adapter was ligated to the SphI and ScaI cut human OB-R cDNA to regenerate residues 39, 40 and 323.

The substitution mutant (420–496)TO(500–632) was constructed as follows. A PCR product was generated using the human leptin receptor cDNA as template and two oligonucleotide primers (5' GAACATGAATGCCATTTCCAGC-CAATCTTCCTATTATC (SEQ.ID.NO:7) and 5' GGAAAATGCATTCAACTGTGTAGGC-TGGATTGCTC (SEQ.ID.NO:8) which amplified the region encoding residues 500–632. This PCR fragment was cleaved by restriction enzyme BsmI. In a parallel experiment, the full length cDNA encoding the wild type human OB-R was inserted into the expression vector pcDNA3 (Invitrogen). This plasmid was cleaved by BsmI at residues 419 and 499, followed by ligation with the PCR fragment encoding residues 500–632.

The deletion mutant D(867–1165) was constructed as follows. A PCR fragment encoding residues 500–866 was generated using the human OB-R cDNA as template and two oligonucleotides (5' TTCCAGCCAATCTTCCTATTATC (SEQ. ID NO:9) and 5' GACATCTCTAGACATTCTTTG-GTGTGATATTAATAATG (SEQ. ID NO:10). This PCR fragment was cleaved with restriction enzymes EcoNI and XbaI. In parallel, the plasmid pcDNA3 with the human leptin receptor cDNA insert was cleaved with EoNI at residue 640 and with XbaI downstream from the stop codon. The DNA encoding residues 640–1165 was removed by gel purification, and the remaining receptor DNA in the pcDNA3 plasmid was ligated with the PCR fragment encoding residues 640–866.

EXAMPLE 2
Cell Culture

COS cells, a monkey kidney cell line, were maintained in Dulbecco-modified Eagle Medium (DMEM) (Gibco/BRL, Gaithersburg, Md.), 10% bovine calf serum, 50 $\mu$g/ml streptomycin, and 50 U/ml penicillin (growth medium) at 37° C. in an atmosphere of 95% air, 5% $CO_2$. Cells were seeded at approximately $4 \times 10^4/cm^2$ and passaged before confluence.

EXAMPLE 3
Transfection of COS Cells

Eighteen hours before transfection, cells were plated at $3.5 \times 10^5$ cells per 35 mm tissue culture dish. For binding assay, the plasmid encoding the OB-R mutant (500 ng) was transfected.

For luciferase assay, the plasmids AH32 (described below), OB-R mutants and pCH110 (300 ng each) were introduced into cells using liposome-mediated transfection. The plasmid pCH110 was obtained from Promega (Madison, Wis.). Specifically, plasmid or plasmid combination was added to 100 $\mu$l of Optimem™ (Gibco/BRL, Gaithersburg, Md.). Ten $\mu$g of Lipofectamine™ (Gibco/BRL, Gaithersburg, Md.) was added to a second 100 $\mu$l volume of Optimem™. The two solutions were mixed, incubated at room temperature for 30 minutes and total volume adjusted to 1000 μl with Optimem™. Cells were washed twice with phosphate buffered saline. The DNA-liposome complex was applied to cells. Cells were incubated for 6 hours at which time 1 ml of growth medium was added to cells. Sixteen hours later, the transfection mixture was removed and 2 ml fresh growth medium was added.

AH32, an expression vector transactivated by leptin, was constructed as follows. Two complimentary oligonucleotides containing the Stat Binding Element (SBE) from the IRF-1 gene (Sims et al., 1993 *Mol Cell Biol.* 13:690–702; and Pine et al., 1994 *EMBO J.* 13:158–167; both of which are hereby incorporated by reference) were synthesized, kinased and annealed using standard molecular biology techniques (Sambrook et al., 1989 *Molecular Cloning: A Laboratory Manual*, 2nd Ed, Cold Spring Harbor Laboratory Press, Cold Spring Harbor, N.Y.). The sequences of the oligonucleotides used is 5'-CTGATTTCCC CGAATGACG-3' and 5'-CGTCATTTCG GGGAAATCAT-3'. The double stranded oligonucleotides were cloned into a Sma I site of pTKLuc. Plasmid pTKLuc contains a promoter sequence from −35 to +10 of the herpes simplex virus thymidine kinase gene (McKnight et al., 1982 *Science*, 217:316–324) upstream of the firefly luciferase gene found in pZLuc (Schadlow, et al., 1992 *Mol. Biol Cell* 3:941–951). The ligated DNA was used to transform *E. coli* using DH5α competent cells (Gibco/BRL, Gaithersburg, Md.). DNA obtained from the transformed colonies was analyzed by restriction digest analysis and the orientation and number of copies of SBE oligonucleotides found in each of the transformants was confirmed by sequencing through the insert using a sequencing kit (US Biochemical, Cleveland, Ohio). Clone AH32 was found to contain 3 copies of the SBE inserted in the same orientation and was used for further studies with a human fibroblast cell line (WI-38 VA13 subline 2RA; ATCC No. CCL 75.1). Cells transfected with the AH32 showed a 6–10 fold increase in the luciferase activity after 6h of treatment with IFN-α or IFN-γ.

EXAMPLE 4

Luciferase Assay

Approximately 24 hours after transfection, various amounts of recombinant human leptin were added to cells. Cells were then incubated for 24 hours. Cell culture medium was removed and cells were washed promptly with 2 ml of ice-cold calcium and magnesium-free phosphate buffered saline. Cells were then prepared for assay with 150 μl Promega reporter lysis reagent (Promega, Madison, Wis.) according to the manufacturer's protocol. 20 μl of cell lysates was then assayed for luciferase activity using a Dynatech ML 3000 luminometer (Dynatech, Chantilly, Va.) using cycle mode after initiating the reaction with 100 μl of Promega luciferase assay reagent. The β-galactosidase activity in 50 μl of each cell lysate was determined using a β-galactosidase assay (Promega, Madison, Wis.). Results were normalized by dividing the relative light units obtained for each sample by the β-galactosidase activity. Results are shown in FIG. 4.

EXAMPLE 5

Binding Assay

Figure 1:
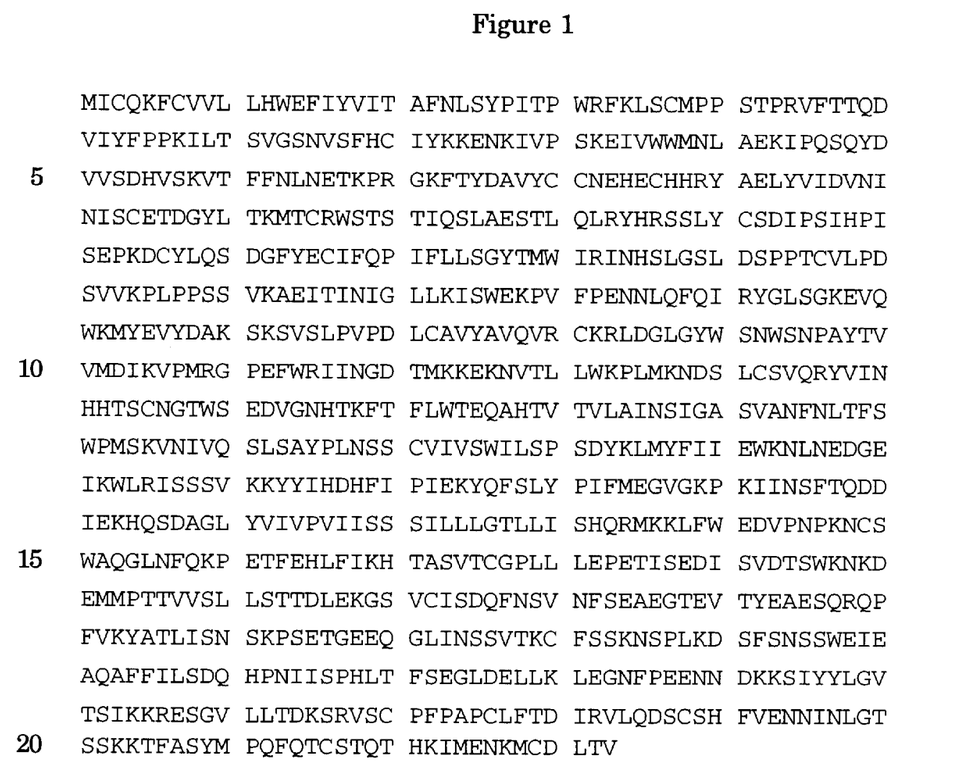
FIG. 1 is the amino acid sequence of a deletion mutant receptor D(41–322) (SEQ.ID.NO:1).
Figure 2:
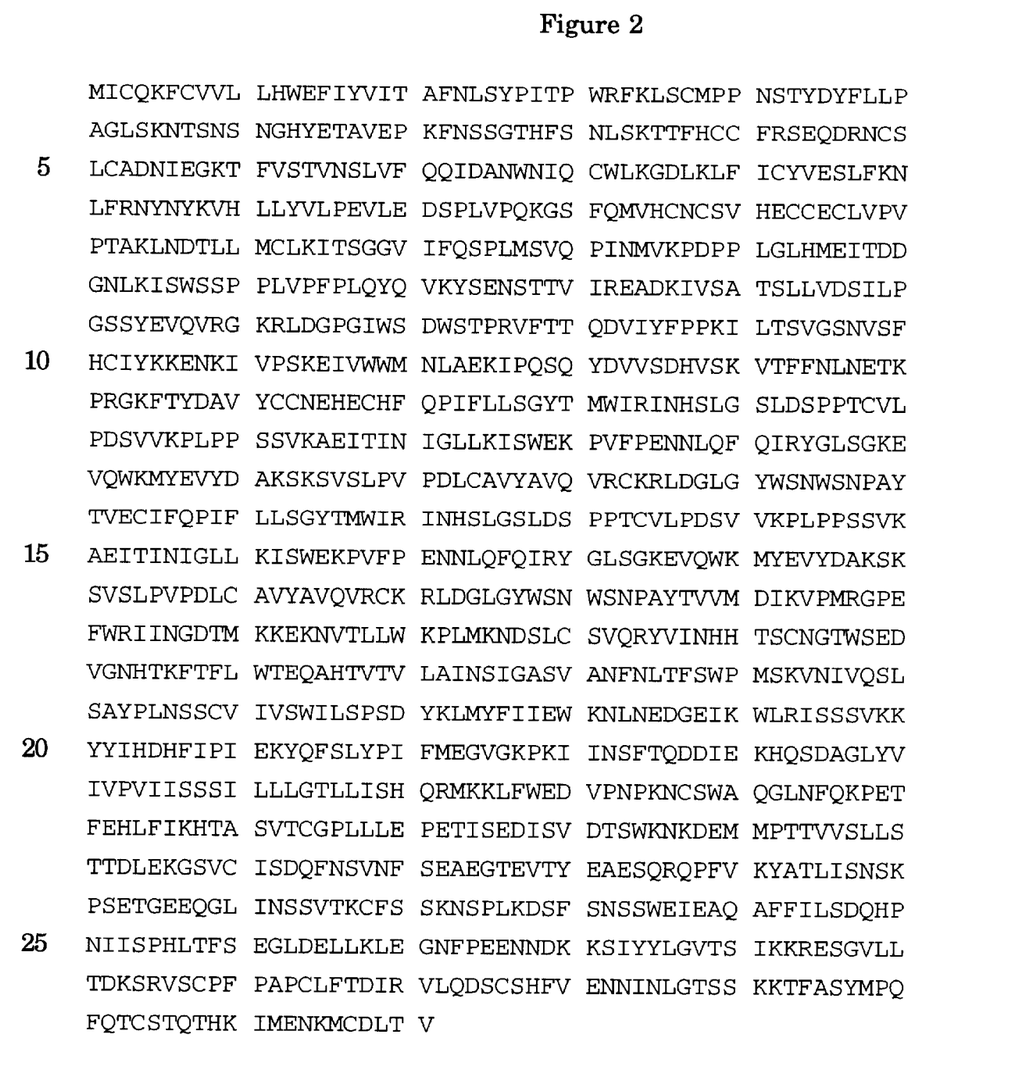
FIG. 2 is the amino acid sequence of a replacement mutant receptor wherein amino acids 420–496 have been deleted and substituted with amino acids 500–632 (SEQ.ID.NO:2).
Figure 3:
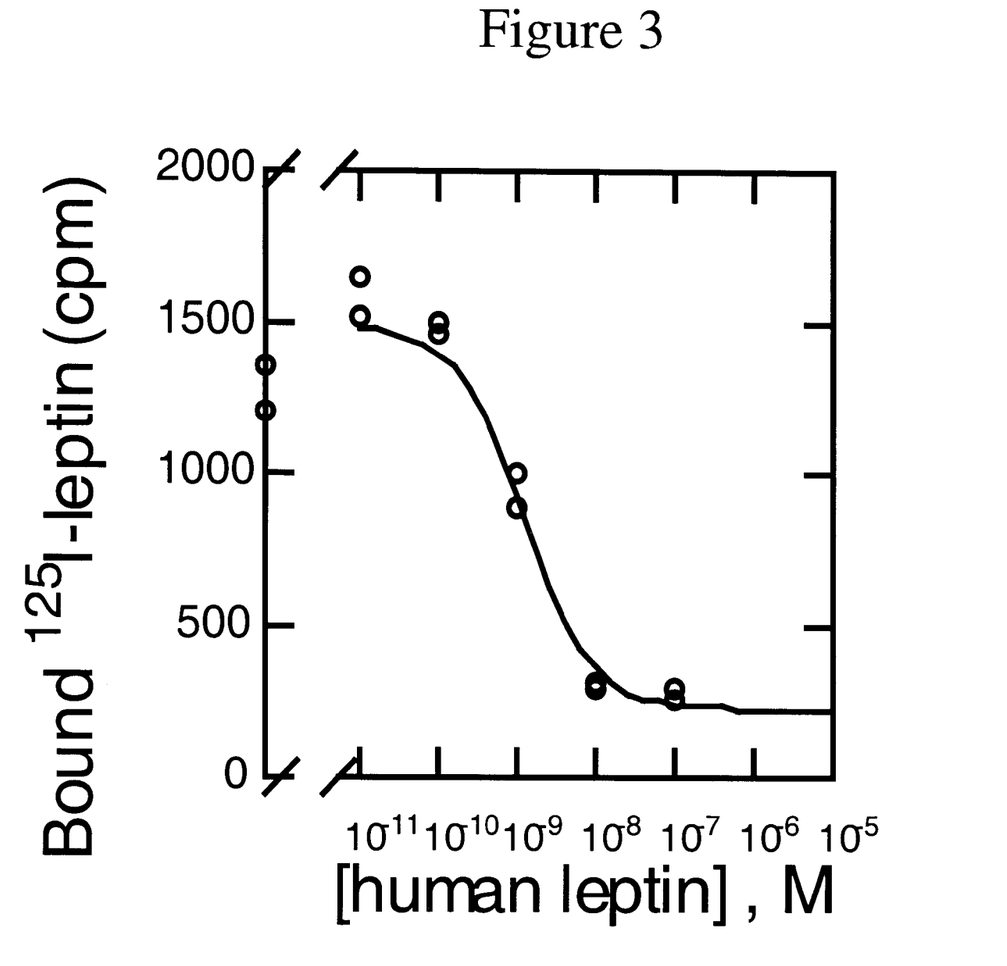
FIG. 3 is a graph of a binding assay using the deletion mutant of FIG. 1.

Approximately 36 hours after transfection, the culture dish was washed with binding buffer (Hank's balanced salt solution supplemented with 0.5% BSA-25 mM HEPES-0.5% NaN3). $^{125}$I-leptin (NEN, Boston, Mass.) was diluted to 0.2 nM in the binding buffer, and 0.5 ml was added to each well. Unlabeled leptin was added to the final concentrations ranging from 10 pM to 10 nM. The cells were incubated at room temperature for 3 hours, after which the cells were washed with the binding buffer 4 times and lysed with 0.1% SDS. The cell lysate was counted in gamma counter. Results are shown in FIG. 3.

---

What is claimed is:

1. A mutant ob receptor which differs from a wild-type receptor by reason of a deletion of amino acid residues which comprise all or substantially all of the first CK-F3 module.

2. A method for determining if an OB-R ligand is present in a sample comprising:

(a) contacting a cell with the sample, wherein the cell expresses an OB-R of claim 1; and     (b) determining if binding occurs wherein binding indicates that an OB-R ligand is present in the sample.

3. A nucleic acid which encodes a receptor of claim 1.

4. A vector comprising a nucleic acid of claim 3.

5. A host cell comprising a receptor of claim 1.

6. A host cell according to claim 5 further comprising a reporter gene construct comprising a leptin response element operatively linked to a reporter gene.

7. A receptor according to claim 1 which comprises SEQ ID NO: 1.

8. A method for determining if an OB-R ligand is present in a sample comprising:

a) contacting a cell with the sample wherein the cell expresses a mutant OB-R lacking all or substantially all of the first CK-F3 module; and wherein the cell also comprises a reporter gene construct comprising a leptin response element operatively linked to a reporter gene; and     b) determining if transcription or translation of the reporter gene occurs wherein transcription or translation indicates an OB-R ligand is present in the sample.

9. A method according to claim 8 wherein the cell expresses an OB-R mutant which contains a deletion of amino acid residues which comprise all or substantially all of the first CK-F3 module.

10. A method according to claim 9 wherein the leptin response element is an IRF-1 derived gamma-interferon activation sequence.

11. A method according to claim 10 wherein translation of a luciferase reporter gene is determined.

* * * * *